(12) United States Patent
Panchal et al.

(10) Patent No.: US 9,174,920 B1
(45) Date of Patent: Nov. 3, 2015

(54) INTEGRATED PROCESS OF DISTILLATION WITH SIDE REACTORS FOR SYNTHESIS OF ORGANIC ACID ESTERS

(71) Applicants: E3TEC SERVICE, LLC, Clarksville, MD (US); BOARD OF TRUSTEES OF MICHIGAN STATE UNIVERSITY, East Lansing, MI (US)

(72) Inventors: Chandrakant B. Panchal, Clarksville, MD (US); John C. Prindle, Baton Rouge, LA (US); Aspi Kolah, Mason, MI (US); Dennis J. Miller, Okemos, MI (US); Carl T. Lira, East Lansing, MI (US)

(73) Assignees: E3TEC Service, LLC, Clarksville, MD (US); Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 14/517,325

(22) Filed: Oct. 17, 2014

Related U.S. Application Data

(60) Provisional application No. 61/961,526, filed on Oct. 17, 2013.

(51) Int. Cl.
*C07C 67/08* (2006.01)
*B01D 3/00* (2006.01)

(52) U.S. Cl.
CPC ............... *C07C 67/08* (2013.01); *B01D 3/009* (2013.01)

(58) Field of Classification Search
CPC .......... C07C 67/08; B01J 2219/00; B01J 3/00
USPC ............................. 568/179, 204; 422/187, 610
See application file for complete search history.

(56) References Cited

U.S. PATENT DOCUMENTS 7,667,068 B2   2/2010   Miller et al.

OTHER PUBLICATIONS

Kolah et al, "Triethyl Citrate Synthesis by Reactive Distillation," Ind. Eng. Chem. Res. (2008), 47, 1017-1025.
Bizzari et al, "Plasticizers," CEH Marketing Research Report, Chemical Economics Handbook—SRI Consulting, Nov. 2009.
Malveda et al, "Citric Acid," CEH Marketing Research Report, Chemical Economics Handbook—SRI Consulting, Nov. 2009.
Taylor and Krishna, "Modelling Reactive Distillation," Chemical Engineering Science, 55 (2000), 5183-5229.
DeGarmo et al, "Consider Reactive Distillation," Chemical Engineering Progress, 88, 43-50, Mar. 1992.
Krishna, "Reactive Separations: More Ways to Skin a Cat," Chemical Engineering Science, 57 (2002), 1491-1504.
"Reactive Distillation," Sundmacher and Kienle, eds., 2002.
Baur and Krishna, "Distillation Column with Reactive Pump Arounds: An Alternate to Reactive Distillation," Chemical Engineering and Processing, 43 (2003), 435.
Schoenmakers and Buhler, "Distillation Column with External Reactors—An Alternate to the Reaction Column," Chemie Ingenieur Technik, 54 (1982) Nr. 2, 163 (untranslated).
Jakobsson et al., "Modeling of Side Reactor Configuration Combining Reaction and Distillation," Chemical Engineering Science, 57 (2002), 9, 1521-1524.
Huang and Vane., "BioSep: A New Ethanol Recovery Technology for Small Scale Rural Production of Ethanol from BioMass," AIChE Presentation, San Francisco, CA, Nov. 2006.
AIChE Smart Brief, 2011.
Consumer Product Safety Improvement Act of 2008, Public Law 110-314, 2009.

*Primary Examiner* — Sikarl Witherspoon
(74) *Attorney, Agent, or Firm* — Rosenberg, Klein & Lee

(57) ABSTRACT

An integrated process and system for synthesis of organic-acid esters is provided. The method of synthesizing combines reaction and distillation where an organic acid and alcohol composition are passed through a distillation chamber having a plurality of zones. Side reactors are used for drawing off portions of the composition and then recycling them to the distillation column for further purification. Water is removed from a pre-reactor prior to insertion into the distillation column. An integrated heat integration system is contained within the distillation column for further purification and optimizing efficiency in the obtaining of the final product.

37 Claims, 5 Drawing Sheets

INTEGRATED PROCESS OF DISTILLATION WITH SIDE REACTORS FOR SYNTHESIS OF ORGANIC ACID ESTERS

RELATED PATENT APPLICATIONS

This Application claims priority to U.S. Provisional Patent Application Ser. No. 61/961,526, filed on 17 Oct. 2013, and is hereby incorporated by reference.

STATEMENT REGARDING FEDERALLY SPONSORED RESEARCH OR DEVELOPMENT

This invention was made with government support under DE-SC0008290 awarded by the U.S. Department of Energy. The government has certain rights in the invention.

FIELD OF THE INVENTION

This method and system relates to an integrated distillation process with side reactors and water separation units for manufacture of industrial chemicals. In particular, this system and method relates to an integrated distillation process which provides for a reactive distillation column having a multiplicity of zones through which a pre-reacted alcohol and organic acid composition is passed.

Still further, this invention relates to a system and method for synthesizing organic-acid esters where the distillation column includes a plurality of zones where a portion of the composition is removed in a side-draw for passage through side reactors.

Still further, this invention pertains to a system and method for synthesizing organic acid esters where the drawn portion of the composition reacted in side reactors is heated for recycling of a vapor stream into an overhead vapor stream of the distillation column and simultaneously returning a liquid stream to a zone of the distillation chamber below the zone from which the side draw was transported to the side reactors. Further, this invention relates to a system and method for synthesizing organic-acid esters where particular zones within the distillation column include heat integration systems where heated liquid from heaters are returned to a zone for passage through heat exchange tubes for controlling the temperature parameters of the distillation system.

Further, the subject system and method for synthesizing organic-acid esters includes reboilers which are contained within the distillation column in predetermined zones for further adjusting temperature parameters between zones of the distillation column.

RELATED PRIOR ART

Esters are synthesized by reacting organic acids with alcohols. Prior art esterification processes having separate chemical reaction and separation processes are generally energy and capital intensive. An integrated process of reactive distillation would combine chemical reaction and separation into a single process unit which would significantly reduce energy consumption and capital costs and is a long needed solution to the problem of synthesizing organic-acid esters.

Eastman Chemical has provided a commercial methyl acetate process with a single step esterification reaction using reactive distillation to perform five functions in one column which has resulted in a 60% reduction of capital expenditure and energy consumption relative to the conventional unit operation design. Application of reactive distillation to esterification of carboxylic acids with multiple acid groups such as citric acid to form tri-ethyl citrate has not been practiced commercially with success. The Michigan State University has developed conventional reactive distillation processes, however, there are challenges of slow reaction kinetics and thermodynamic limitations rendering a traditional unit operation based process with significant disadvantages, and conventional reactive distillation requires extremely large columns and significant energy usage to produce the esters. Thus, advances in reactive-distillation processing are needed to meet the low capital and energy cost requirements necessary for commercial competitiveness.

At the present time, most esters of organic acids are produced batch-wise from multi-step reversible reactions between multi-functional acids and one alcohol, such as tri-ethyl citrate from ethanol or a multi-functional alcohol and one acid, such as isosorbide di-esters. The reversible reactions require an excess of lighter reactant in order to strip off water by-product and drive the reaction to completion. Such batch processes are energy inefficient and require large amounts of the excess reactant and result in a batch-to-batch produce quality variation. Thus, there is the need for a continuous process system and method which provides a uniform product quality with less raw material waste and improved thermal management.

It is not believed that there are any heat integrated distillation side reactor based processes for manufacturing of multifunctional esters such as triethyl citrate. Reactive distillation based multifunctional ester processes have been shown in prior systems published by Michigan State University. The subject method and system of heat integrated distillation side reactor processing with a water separation unit such as a PerVap membrane is in direct opposition with the conventional process of separate reaction and multiple separation and purification steps where the subject system and method includes the recycling of unreacted intermediate products.

Esterification of organic acids with alcohols produce water, which induces reverse reactions and thereby limits conversion to chemical equilibrium. In order to minimize such reverse actions, excess reactant with higher volatility (either alcohol or organic acid) is used to carry water to the overhead of the distillation column which requires vaporization in the column and subsequent condensation in the overhead condenser resulting in a high energy consumption and larger distillation column. The subject system is based on the application of a water separation unit such as a PerVap or molecular sieve bed or another standard type aqueous/organic phase separator to separate product water from the effluent streams of a pre-reactor as well as side reactors in an integrated process of permeation and evaporation.

DESCRIPTION OF THE PREFERRED EMBODIMENTS

Figure 1:
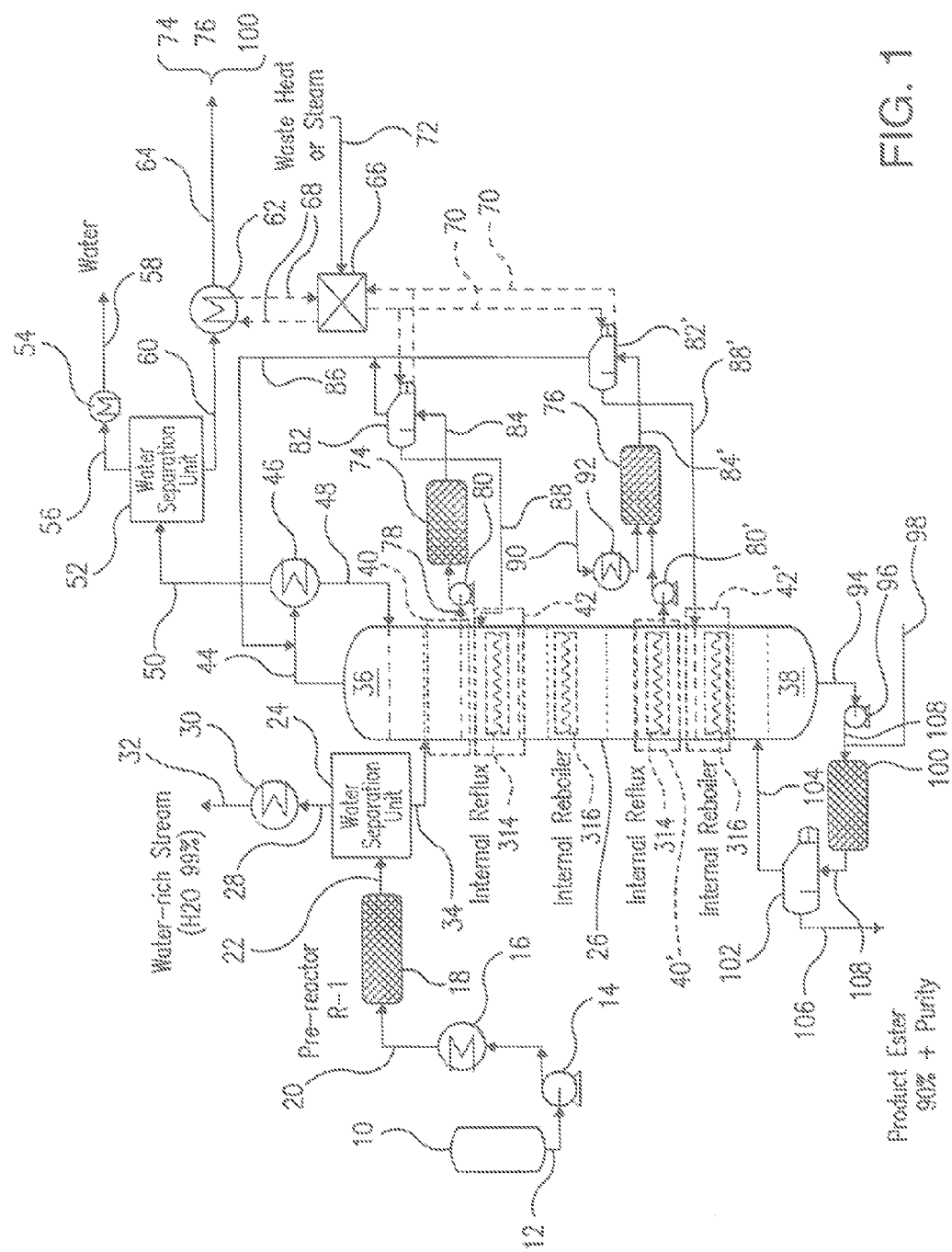
FIG. 1 is a schematic flow diagram of the system and method for synthesizing organic-acid esters.

Referring now to FIG. 1, there is shown an integrated process for manufacturing of esters of organic acids through the reaction of organic acid esterification with alcohol. An alcohol and organic composition is contained in tank 10. The alcohol and organic acid composition is drawn through tank line 12 by pump 14 and possibly preheated in preheater 16 prior to insertion into pre-reactor 18 on line 20.

In general, the subject process and system is adaptable to a wide range of alcohols and is particularly directed for use with ethanol, butanol, hexanol, 2-ethyl hexanol, 3,5,5-trimethylhexanol, nonyl alcohol, isonyl alcohol, tridecanol, methanol, benzyl alcohol and isosorbide.

Similarly, the organic acid may be chosen from organic acids such as citric acid, adipic acid, succinic acid, 1,4-cyclohexane dicarboxylic acid, 1,2-cyclohexane dicarboxylic acid and a mixture of fatty acids derived from vegetable oils.

Reaction of the alcohol and organic acid composition is provided in pre-reactor 18 which is maintained at a predetermined temperature and pressure, dependent upon the parameters and composition of the alcohol and organic acid to provide a reaction product mixture of alcohol and organic acid. Such pre-reactors 18 are well-known in the art and provide for reaction of the inserted composition. The reaction product mixture is then passed on pre-reactor line 22 to first water separation unit 24.

First water separation unit 24 may provide for a PerVap membrane, a molecular sieve bed, or another standard type aqueous/organic phase separator. First water separation unit 24 effectively separates water from the pre-reactor 18 effluent or reaction product mixture which permits a sufficient quantity of excess, unreacted reactant (alcohol) which leaves water separation unit 24 to enter the distillation column 26, as will be described in following paragraphs.

First water separation unit 24 serves to separate water from pre-reactor 18 effluent and a vapor and liquid stream of water is passed on first water separation unit outflow line 28 to first condenser 30 for removal of a water-rich stream on condenser effluent line 32. Unreacted alcohol which has not been reacted in pre-reactor 18 in combination with the organic acid is inserted into distillation column 26 on water separation unit line 34. Distillation column 26 consists of a plurality of zones which include upper distillation zone 36 and bottom or lower distillation column zone 38 with intermediate distillation zones represented in FIG. 1 by elements 40, 40', 42 and 42'. Only two intermediate zones will be discussed in general for clarity purposes. However, it is to be clearly understood that distillation column 26 may include a plurality of first and second representative distillation column zones 40 and 42.

Upon entry of unreacted alcohol and organic acid into upper distillation column zone 36 on water separation unit line 34, there is a mixture of liquid and vapor. A column vapor stream is removed on overhead vapor line 44 and inserted into second condenser 46 which condenses the column vapor stream in overhead vapor line 44 into a liquid stream on second condenser output line 48 for reinsertion into upper distillation column zone 36 for passage through the representative first and second distillation column zones 40 and 42.

The vapor residual is passed on vapor effluent condenser line 50 for insert into second water separation unit 52 which as was the case for first water separation unit 24 may be a PerVap membrane, a molecular sieve bed, or other type of standard aqueous/organic phase separator. Water is drawn from second water separation unit 52 on output line 56 to third condenser 54 for condensing the vapor into a water rich stream on third condenser line 58. Water separated overhead vapor line 60 passes from second water separation unit 52 to fourth condenser 62 with excess reactant alcohol being passed on fourth condenser line 64 to be passed to representative side reactors 74, 76, 100 to be further discussed in following paragraphs.

Thermal heat pump 66 is used for recovery of latent heat of condensation from vapor stream on line 60 for use in intermediate heat exchangers to be discussed in following paragraphs. A commercially available refrigerant pair such as ammonia/water mixture or other organic pairs may be used in thermal heat pump 66. Refrigerant 68 recovers the latent heat of condensation and transfers upgraded heat at higher temperatures as represented by upgraded heat transfer lines 70 to the intermediate heat exchangers. Refrigerant 68 recovers the heat and transfers the upgraded heat at higher temperature to the overall process by using the upgraded heat within the intermediate heat exchangers. Thermal heat pump 66 may be operated by waste heat transferred to it on line 72 which is generally available in a commercial plant. Thermal heat pump 66 significantly improves the overall efficiency by recovering and utilizing latent heat from the vapor stream which otherwise would be rejected to cooling water or the external environment.

Further referring to FIG. 1, there is provided top side reactor 74 and intermediate side reactor 76 which is representative of one or more side reactors in the distillation column 26. Only two side reactors 74 and 76 are shown for clarity purposes. The reaction mixture being inserted into distillation column 26 on water separation unit line 34 passes into first representative upper distillation column zone 40 a portion of which is passed on zone output line 78 to second pump 80 for insertion into top side reactor 74. A further reaction is provided in top side reactor 74 with the reacted composition being inserted into first heat exchanger 82 by passage on first heat exchanger input line 84. As is seen, thermal heat pump 66 provides additional heat to first heat exchanger 82 for increasing the overall efficiency of the process. Once the effluent from top side reactor 74 is heated, heat exchanger 82 passes the vapor stream on heat exchanger output line 86 to overhead vapor line 44 for insertion into second condenser 46 in a recycling process.

Heat exchanger 82 heats the liquid to both a vapor and a liquid portion where the liquid portion is inserted on line 88 to a next sequentially lower zone 42 for further reaction within distillation column 26.

Intermediate zones 40' and 42' operate in substantially the same process mode as that provided for first representative upper distillation column zone or top zone 40 with the exception that intermediate side reactors represented by intermediate side reactor 76 provides for fresh and recycled or recovered excess reactant (alcohol) being inserted on recycle line 90 for passage through a fifth condenser 92 prior to insertion into intermediate side reactor 76. The reacted composition inside reactor 76 will then pass through line 84' to heat exchanger 82' and then pass the vapor on heat exchanger output line 86 back to overhead vapor line 44. The liquid portion of the heat exchanger effluent is then passed on heat exchanger liquid line 88' to second representative intermediate zone 42'.

The distilled reactant is passed to bottom or lower distillation column zone 38 subsequent to passage through distillation column 26. Distillation reactant line 94 draws off the reacted and distilled composition through distilled reactant line 94 to be pumped by third pump 96 into line 108 where it is combined with recycle line 98 which carries fresh and recycled or recovered excess reactant (alcohol) for insertion into product side reactor 100 for passage to product heat exchanger 102 on line 108. Vapor stream from heat exchanger 102 is passed on vapor product line 104 back to distillation column 26 into bottom or lower distillation column zone 38. Product line 106 then provides for the product ester of high purity on line 106.

Of importance is the use of first water separation unit 24 which effectively separates the water from the pre-reactor 18 effluent or reaction product mixture which allows a sufficient quantity of excess, unreacted reactant (alcohol) leaving the pre-reactor 18 to enter distillation column 26 and subsequently and initially being fed to first side reactor 74 which reduces or eliminates the requirement of additional excess reactant (alcohol) to be fed to the side reactor 74. By effectively separating product water on line 32 subsequent to pre-reaction in pre-reactor 18, the process energy consumption is reduced by more than 40%. Further reduction may be possible by implementing an additional water separation unit 24 in the excess reactant (alcohol) recovery process.

Table I represents the improvements when a water separation unit 24 (in the form of a PerVap membrane) is inserted between the pre-reactor 18 and distillation column 26. The Table is depicted for reaction of citric acid esterification with ethanol.

TABLE I

| Item | Process Parameter | With Separation of Water from Pre-reactor Product Stream and Overhead Product | With Water Separation of Pre-reactor Product Stream | Without Water Separation Units |
|---|---|---|---|---|
| 1 | Production Capacity | 40.0 KTA | 40.0 KTA | 40.0 KTA |
| 2 | Feed Rate - 25% citric acid in ethanol | 10,616 kg/hr | 10,460 kg/hr | 10,460 kg/hr |
| 3 | Recycled ethanol feed to side reactors | 3,063 kg/hr | 3,500 kg/hr | 6,230 kg/hr |
| 4 | Product Stream | | | |
| 5 | Flow rate | 5,485 kg/hr | 5,495 kg/hr | 5,460 kg/hr |
| 6 | Tri-ethyl concentration | 90% by wt | 90% by wt | 90% by wt. |
| 7 | Product yield based on citric acid | 96% by mol. | 96% by mol. | 96% by mol. |
| 8 | Side Reactors | | | |
| 9 | Temperature | 107° C. | 105° C. | 105° C. |
| 10 | Pressure | 2.5 atm | 2.5 atm | 2.5 atm |
| 11 | Distillation columnn | | | |
| 12 | Reflux temperature | 107° C. | 103° C. | 105° C. |
| 13 | Bottom temperature | 150° C. | 148° C. | 105° C. |
| 14 | Energy Consumption | 3,080 kW | 5,985 kW | 10,255 kW |
| 15 | Synthesis process | 2,520 kW | 2,520 kW | 4,160 kW |
| 16 | Ethanol recovery unit - distillation | | 3,465 kW | 6,095 kW |

In the overall process, heat integration is an important part of the concept for increasing energy efficiency and maintaining optimum conditions while minimizing adverse impacts of process condition perturbations, such as changes in reflux ratio or condenser temperature to maximize conversion and separation. As has previously been discussed in FIG. 1, latent heat liberated in condensing the overhead vapor passing from upper distillation column zone 36 may be recycled into intermediate reboilers or heat exchangers 82, 82', using the thermal heat pump 66.

It is to be noted that the latent heat of condensing the overhead vapor may also be recycled using a thermal or mechanical vapor recompression heat pump. In a particular instance, the use of a thermal heat pump such as 66, has been shown to reduce energy consumption in hydrogen peroxide distillation by up to 56%. As is always the case, the relative economics between a mechanical vapor recompression heat pump and a thermal heat pump would depend on comparative costs of electricity, steam, or recovery of available waste heat.

Internal heat integration units 314 focus on process controls by maintaining parameters within an optimum operating temperature envelope. Internal heat integration may be provided by providing cooling as singular or multiple heat integration units or multiple internal refluxes 314. Internal reboilers 316 may be incorporated as shown in FIG. 1 in one or more distillation zones of distillation column 26. Such internal reboilers 316 provide heat as necessary for the obtaining of optimum temperature profiles of the distilling composition.

Prior art distillation processes are generally controlled by monitoring temperatures and pressures as well as minor fluctuation in the process parameters by compensation through use of linear programming methods. With the use of side reactors such as 74 and 76, the interactive effects of reaction and separation require a new generation of process controls and thermal management within distillation column 26. The subject process is unlike the governing of temperature profiles by boiling points of top and bottom products. This concept process is governed by the product streams from side reactors such as 74 and 76. In order to maintain predetermined temperature profiles for particular compositions, internal heat integration is required with external feedback controls.

Figure 2:
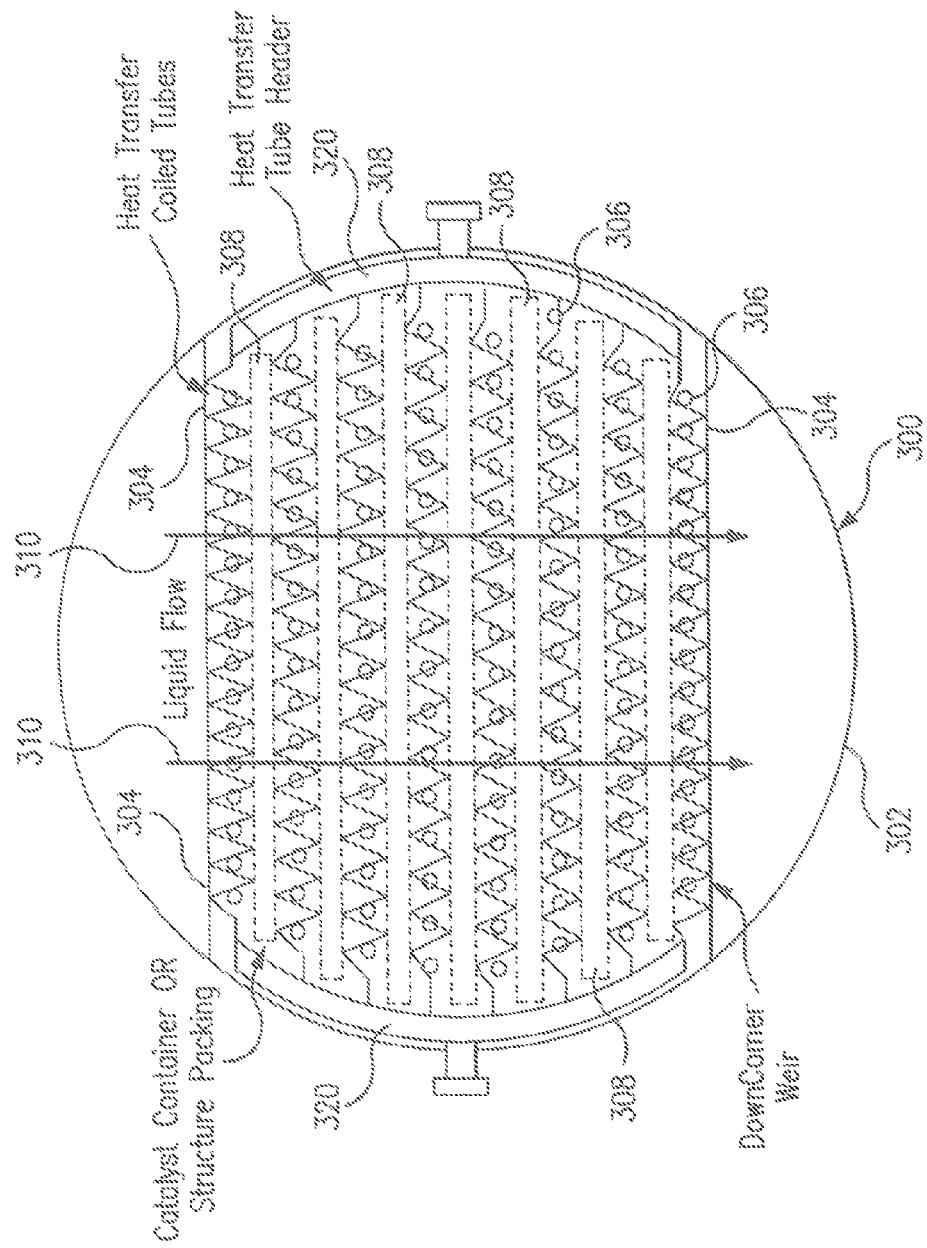
FIG. 2 is a schematic drawing of a heat integration system contained within a distillation column of the subject invention.

Referring now to FIG. 2, there is shown a schematic view of a representative heat integration system 300 mounted internal to distillation column 26 in a predetermined zone or zones. Heat integration system 300 may include sieve or valve distillation tray 302 with liquid flow passing in liquid flow direction 310. Catalyst containers 308 are mounted or sandwiched between heat transfer coiled tubes 306 as provided in FIG. 2. Heat transfer tube headers 320 are provided with the weirs 304 established on opposing ends of the rows of heat transfer coil tubes 306 and the sandwiched catalyst containers 308.

Figure 3A:
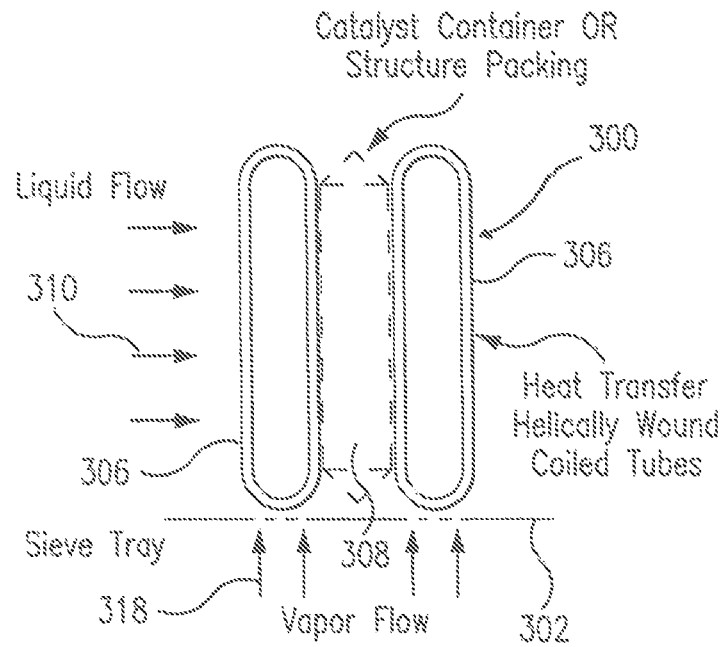
FIG. 3A is a schematic drawing of a heat integration system mounted on a distillation tray within a distillation column where catalyst containers are mounted between heat transfer coiled tubes.
Figure 3B:
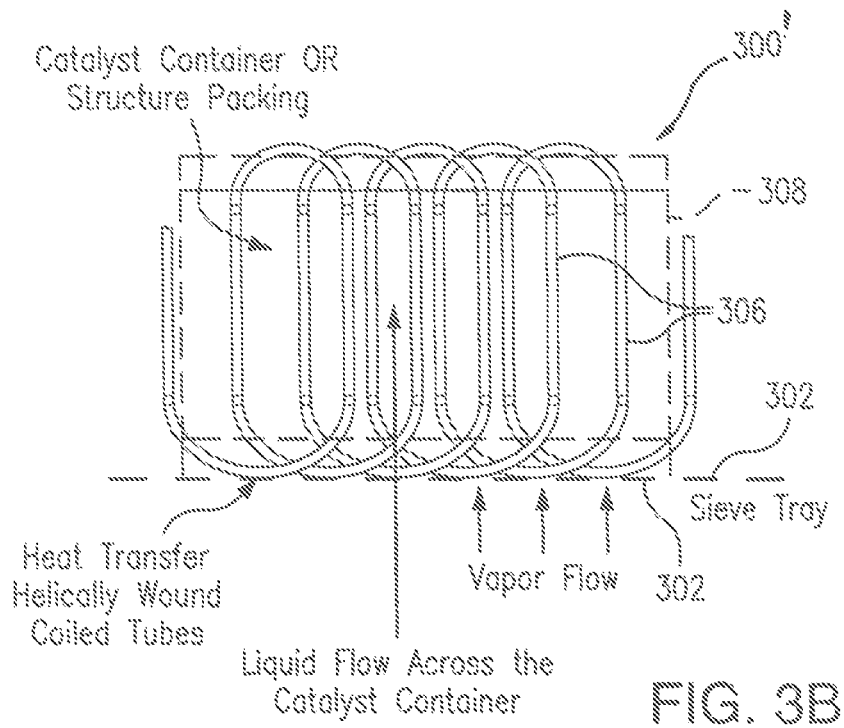
FIG. 3B is directed to an embodiment of the heat integration system showing heat transfer helically wound coiled tubes embedded within a catalyst container or structure packing which are mounted on distillation trays within the distillation column.

FIGS. 3A and 3B schematically show two forms of heat integration system 300. FIG. 3A provides for heat transfer coil tubes 306 for transporting heat from tubes 306 to catalyst container 308 with a liquid flow direction 310 where catalyst containers 308 are sandwiched between sequentially mounted tubes 306. Vapor flow passes in direction 318 with liquid flow in direction 310 for passage over heat transfer coil tubes 306.

In another type of heat integration system 300', coil tubes 306 as shown in FIG. 3B are provided as being embedded within catalyst containers 308 mounted on sieve or valve distillation trays 302. Alternatively, catalyst container 308 may be mounted internal the helically wound heat transfer tubes 306.

Figure 4:
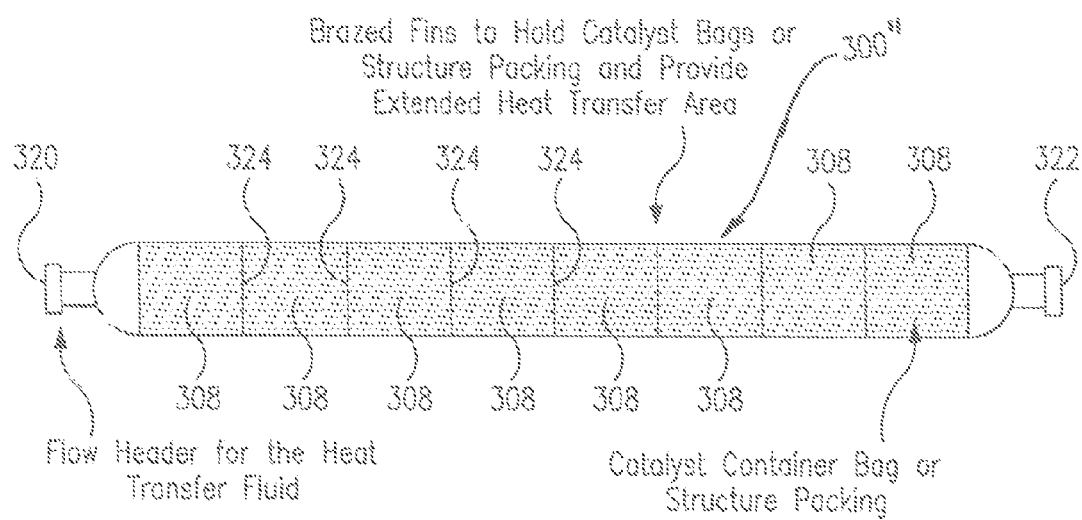
FIG. 4 is a schematic drawing showing brazed fins for holding catalyst bags or structure packing where the heat transfer fluid is passed through the catalyst containers; and, FIG. 5 is a schematic flow diagram showing the system and method for a commercial plant in the synthesis of organic-acid esters.

Referring to FIG. 4, there is shown a further embodiment of heat integration system 300" which provides for a system whereby catalyst container bags 308 are mounted on sieve distillation tray 302 and include a plurality of brazed fins 324 to hold the catalyst containers 308 while providing for an extended heat transfer area. Input flow header 320 provides for the entry of the heat transfer fluid and output flow header 322 returns the heat transfer fluid to the process system.

Figure 5:
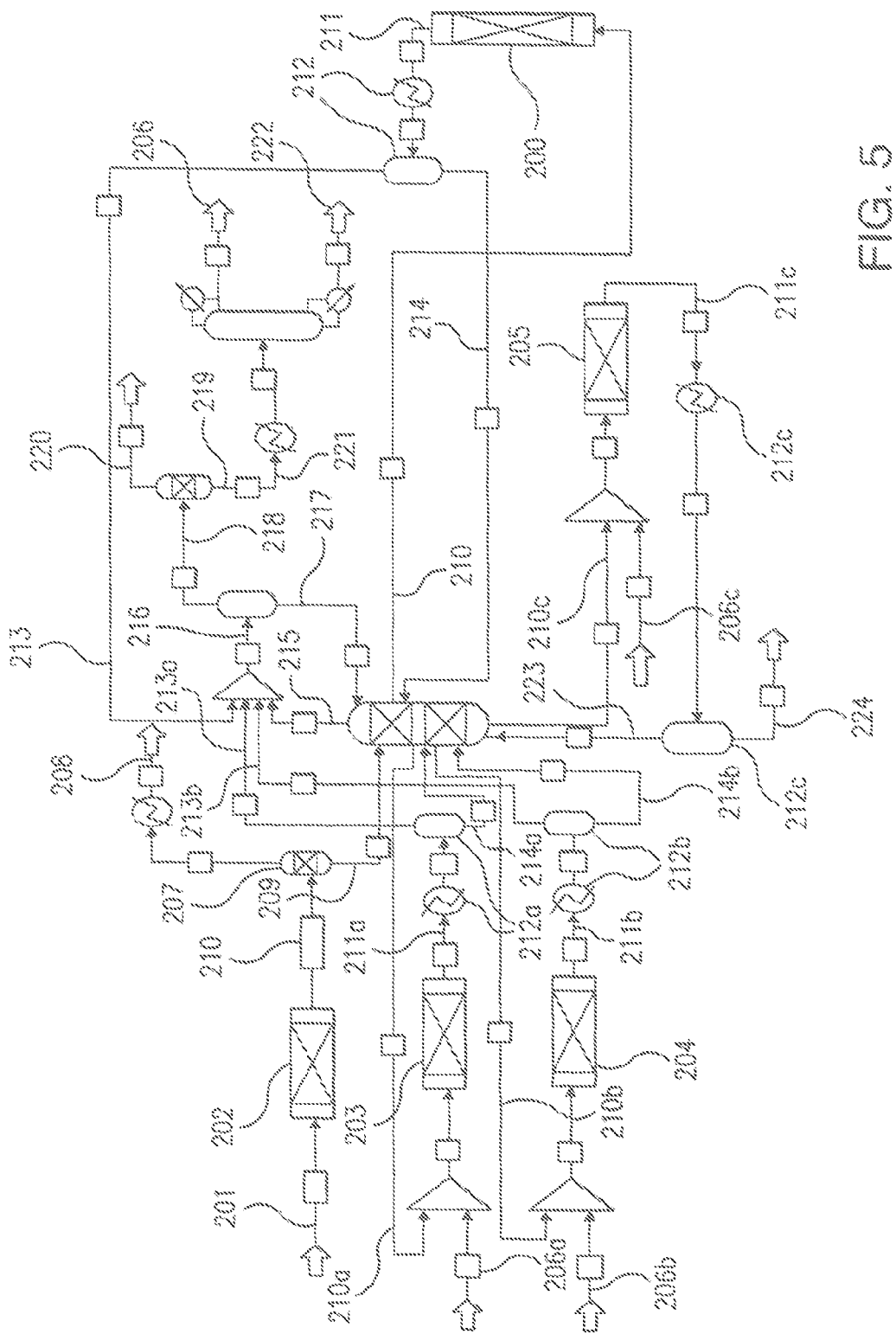

Process design of a commercial distillation plant is shown in FIG. 5 with design parameters for a 40,000 tons per annum commercial plant as shown in Table I. Feed enters through stream line 201 and is reacted in pre-reactor 202 to produce a reaction product mixture. Reactor effluent 210 is fed to Per-Vap membrane 207 where water produced in the reaction in the pre-reactor 202 is removed and condensed and exits as a condensed water product on line 208. In this example, the alcohol and organic acid composition is ethanol and citric acid. The remaining excess alcohol and citrate esters are also exiting the PerVap unit 207 and enter the distillation column in line 209. As was presented in the process FIG. 1, the heavier esters travel down the column and are removed in side streams and fed to side reactors 200, 203, 204, and 205. In all but the top-most side-stream/side-reactor configuration 200, fresh and/or recycled ethanol 206 is brought back on lines 206a, 206b, and 206c which are combined with the liquid side-draw 210a, 210b, and 210c prior to entering the reactors 203, 204, and 205.

The fresh and/or recycled ethanol stream may be preheated to maintain the reactor feed at desired temperatures. The effluent stream 211a, 211b, and 211c from each of the respective side reactors 203, 204, and 205 are then fed to a reboiler 212a, 212b, 212c where the byproduct water and unreacted ethanol are vaporized prior to the remaining liquid being returned to the column stage or zone below the corresponding side-draw.

For all but the final reboiler 212c, the vapor streams 213, 213a, 213b are combined with the column overhead stream 215. Any triethyl citrate which was partially vaporized from the vapor streams is condensed and returned to the distillation column on line 217 in order to optimize product recovery. The vapor stream 218 is then passed through a molecular sieve for separation of water 220 from the ethanol-rich stream 221. Ethanol may be further concentrated by distillation for separation of by-product diethyl ether 222. Ethanol with a purity of >99 wt % 206 is then recycled into the side reactors. The reboiler 212c from the final side reactor 205 is employed as the column's reboiler and the vapor is returned to the bottom zone of the column through line 223. It has been found that the product stream has a 90 wt % triethyl citrate 224 being withdrawn as a liquid stream from reboiler 212c.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. An integrated process for synthesizing organic acid esters comprising:
   (a) establishing an alcohol and organic acid composition;
   (b) reacting said alcohol and organic acid composition in a pre-reactor to form at least one ester;
   (c) separating water from said alcohol and organic acid composition to form a separated reaction product mixture;
   (d) introducing said separated reaction product mixture into an upper zone of a distillation column, said distillation column having a plurality of distillation zones, said distillation zones arranged in upper and bottom distillation zones, wherein the step of introducing the separated reaction product mixture into said upper distillation zone of a distillation column is followed by the steps of:
      (a1) drawing a liquid side stream from a predetermined zone of said distillation column which is sequentially lower than said upper distillation zone into at least one first side reactor;
      (b1) passing an effluent stream from said first side reactor to a heat exchanger;
      (c1) drawing a vapor stream from said heat exchanger for combining with said overhead vapor stream of said distillation column; and
      (d1) drawing a liquid stream from said heat exchanger for re-introduction into said distillation column;
   (e) drawing a column overhead vapor stream off of said separated reaction product mixture from an upper distillation zone;
   (f) passing said reaction product mixture through a plurality of distillation zones in the distillation column for distilling said organic esters from said introduced separated reaction product mixture liquid; and
   (g) removing enriched organic ester from a bottom distillation zone of said distillation column.

2. The method as recited in claim 1 wherein said reacting step is performed in a pre-reactor being maintained at a predetermined pressure and temperature for producing said reaction product mixture.

3. The method as recited in claim 1 where the step of separating water from the reaction product mixture of said alcohol and organic acid composition includes the step of introducing the reaction product mixture to a first water separation unit for separating water rich vapor from the reaction product mixture of said alcohol and organic acid composition.

4. The method as recited in claim 3 where the step of introducing reaction product mixture of said alcohol and organic acid composition into said first water separation unit is followed by the steps of:
   (a) drawing said water rich vapor from said first water separation unit; and,
   (b) condensing said water rich vapor in a first condenser to provide a water rich liquid stream.

5. The method as recited in claim 3 where the first water separation unit is selected from the group consisting of a PerVap membrane, a molecular sieve, or an aqueous/organic phase separator.

6. The method as recited in claim 1, wherein step (c1) includes the following steps:
   (a) passing said combined vapor stream through a second condenser to produce a saturated vapor stream and a condensed liquid stream;
   (b) drawing said saturated vapor stream from said second condenser; and
   (c) drawing said condensed liquid stream from said first condenser and re-introducing said condensed liquid stream into said upper distillation zone of said distillation column.

7. The method as recited in claim 1, wherein the step of drawing said saturated vapor stream from said second condenser includes the following additional steps:

(a) passing said saturated vapor stream from said second condenser through a second water separation unit for separating a water-rich vapor stream from an alcohol or acid rich stream;

(b) passing said water-rich vapor stream through a third condenser to yield water; and (c) passing said alcohol or acid rich stream through a fourth condenser to produce a liquid stream of excess reactant alcohol or acid introduced to at least one side reactor.

8. The method as recited in claim 1, wherein the heat exchanger is a reboiler.

9. The method as recited in claim 7 including the step of recovering latent heat of condensation from at least one of the group consisting of said second condenser or said fourth condenser and transferring said latent heat of condensation to at least one of said side reactors.

10. The method as recited in claim 1 where the step of drawing a liquid side stream includes the step of pumping said liquid side stream from said distillation column for charging of said at least one side reactor.

11. The method as recited in claim 1 including the step of maintaining a substantially predetermined temperature profile of said alcohol, organic acid and organic ester mixture in each of said distillation zones.

12. The method as recited in claim 11 where the step of maintaining said substantially predetermined temperature profile includes the step of establishing at least one heat transfer member in at least one of said distillation zones.

13. The method as recited in claim 12 where the step of passing said alcohol, organic acid, organic ester composition through said distillation zones includes the step of locating a catalyst containing member in at least one of said zones.

14. The method as recited in claim 13 where said heat transfer member and said catalyst containing member are integrated into a single unit.

15. The method as recited in claim 1 where the steps of removing said enriched organic ester from said bottom distillation zone of said distillation column includes the step of purifying distilled alcohol and organic acid from said bottom distillation zone of said distillation column.

16. The method as recited in claim 15 where the step of purifying includes the steps of:

(a) drawing said distilled alcohol and organic acid from said bottom zone of said distillation column;

(b) further reacting said distilled alcohol and organic acid in at least a second side reactor; and (c) heating said reacted organic acid and alcohol composition to produce a further purified ester and a returning vapor stream.

17. The method as recited in claim 15 where said returning vapor stream is charged into said bottom distillation zone of said distillation column.

18. The method as recited in claim 14 where the step of integrating said catalyst containing member and said heat transfer member includes the step of positioning at least one catalyst containing member between or inside helically wound heat transfer tubes.

19. The method as recited in claim 14 where the step of integrating said catalyst containing member and said heat transfer member includes the step of embedding a plurality of heat transfer tubes within said catalyst containing member.

20. The method as recited in claim 7 where the second water separation unit is selected from at least one of the group consisting of a PerVap membrane, a molecular sieve bed, or an aqueous/organic phase separator.

21. The method as recited in claim 1 where the alcohol is selected from at least one of the group consisting of ethanol, butanol, hexanol, 2-ethyl hexanol, 3,5,5-trimethylhexanol, nonyl alcohol, isonyl alcohol, tridecanol, methanol, benzyl alcohol and isosorbide.

22. The method as recited in claim 1 where the organic acid is selected from at least one of the group consisting of citric acid, adipic acid, succinic acid, 1,4-cyclohexane dicarboxylic acid, 1,2-cyclohexane dicarboxylic acid and a mixture of fatty acids derived from vegetable oils.

23. A system for synthesizing organic esters comprising:

(a) a tank containing an alcohol and organic acid composition;

(b) a pre-reactor in fluid communication with said tank for providing a reaction mixture;

(c) a water separation unit for separating water from said reaction mixture;

(d) a reactive distillation column in fluid communication with said water separation unit to receive separated reaction mixture from said water separation unit, said reactive distillation column having a plurality of distillation zones for distilling organic esters from said introduced reaction product mixture.

24. The system for synthesizing organic esters as recited in claim 23 where said water separation unit is in fluid communication with a first condenser for providing a water rich liquid stream.

25. The system for synthesizing organic esters as recited in claim 23 where said water separation unit is selected from the group consisting of a PerVap membrane, a molecular sieve, or an aqueous/organic phase separator.

26. The system for synthesizing organic esters as recited in claim 23 including at least a first side reactor fluidly coupled to at least one of said distillation zones.

27. The system for synthesizing organic esters as recited in claim 26 including a recycling mechanism for recycling a vapor stream of said distillation column and inserting a liquid stream into said distillation column.

28. The system for synthesizing organic esters as recited in claim 27 where said recycling mechanism includes a heat exchange in fluid communication with said first side reactor, said distillation column and said overhead vapor stream of said distillation column.

29. The system for synthesizing organic esters as recited in claim 28 including a heat pump thermally coupled to said heat exchanger.

30. The system for synthesizing organic esters as recited in claim 27 including:

(a) a second condenser for receiving said overhead vapor stream and said vapor stream from said heat exchanger; and (b) a second water separation unit fluidly coupled to said second condenser for emitting a water-rich composition exterior the synthesizing system and returning an alcohol or acid rich stream to a fourth condenser.

31. The system for synthesizing organic esters as recited in claim 23 including at least one interval reboiler in at least one of said distillation zones.

32. The system for synthesizing organic esters as recited in claim 23 including at least one heat integration unit mounted internal to said distillation column.

33. The system for synthesizing organic esters as recited in claim 23 including:

(a) a series of heat transfer tubes positioned in at least one of said distillation zones for receiving a liquid stream from a heat exchanger; and (b) a catalyst container containing a catalyst positioned at a predetermined location with respect to said heat transfer tubes.

34. The system for synthesizing organic esters as recited in claim 33 where said catalyst container containing said catalyst is located between adjacent heat transfer tubes.

35. The system for synthesizing organic esters as recited in claim 33 where said catalyst container is mounted internal to said heat transfer tubes.

36. The system for synthesizing organic esters as recited in claim 33 where said heat transfer tubes are embedded within said catalyst container.

37. The system for synthesizing organic esters as recited in claim 23 including a product side reactor in communication with a bottom distillation zone of said distillation column for reacting a distilled product mixture drawn from said bottom distillation zone.

\* \* \* \* \*